(12) United States Patent
Zhang et al.

(10) Patent No.: US 11,523,991 B2
(45) Date of Patent: Dec. 13, 2022

(54) PLANT SOFT CAPSULE AND PREPARATION METHOD AND APPLICATION THEREOF

(71) Applicant: IVC NUTRITION CORPORATION, Jingjiang Taizhou (CN)

(72) Inventors: Guodong Zhang, Jingjiang Taizhou (CN); Jing Hong, Jingjiang Taizhou (CN); Xudong Xia, Jingjiang Taizhou (CN); Xing Zhang, Jingjiang Taizhou (CN); Jiemao Shi, Jingjiang Taizhou (CN); Chendong Shang, Jingjiang Taizhou (CN); Baorong Ding, Jingjiang Taizhou (CN)

(73) Assignee: IVC NUTRITION CORPORATION, Taizhou (CN)

( * ) Notice: Subject to any disclaimer, the term of this patent is extended or adjusted under 35 U.S.C. 154(b) by 0 days.

(21) Appl. No.: 16/758,728

(22) PCT Filed: Jun. 19, 2019

(86) PCT No.: PCT/CN2019/091929
§ 371 (c)(1),
(2) Date: Apr. 23, 2020

(87) PCT Pub. No.: WO2020/248295
PCT Pub. Date: Dec. 17, 2020

(65) Prior Publication Data
US 2021/0128481 A1 May 6, 2021

(30) Foreign Application Priority Data
Jun. 12, 2019 (CN) .......................... 201910508839.9

(51) Int. Cl.
*A61K 9/48* (2006.01)
*A23L 33/00* (2016.01)
*A61K 47/10* (2017.01)
*A61K 47/36* (2006.01)

(52) U.S. Cl.
CPC ............ *A61K 9/4816* (2013.01); *A23L 33/30* (2016.08); *A61K 9/4808* (2013.01); *A61K 9/4833* (2013.01); *A61K 47/10* (2013.01); *A61K 47/36* (2013.01)

(58) Field of Classification Search
CPC .. A61K 9/4816; A61K 9/4808; A61K 9/4833; A61K 47/10; A61K 47/36; A23L 33/30
See application file for complete search history.

(56) References Cited

U.S. PATENT DOCUMENTS

| 6,528,088 B1 * | 3/2003 | Gilleland ............. C09D 103/06 424/463 |
| 7,189,843 B2 * | 3/2007 | Tsai ......................... A61K 8/73 264/39 |
| 7,807,194 B2 * | 10/2010 | Modliszewski ...... A61K 9/7007 424/490 |
| 9,775,814 B2 * | 10/2017 | Teles ..................... A61K 9/4808 |
| 2002/0081331 A1 * | 6/2002 | Tanner ................. A61K 9/4816 424/451 |
| 2004/0063927 A1 * | 4/2004 | Tsai ....................... C07H 13/12 536/54 |
| 2005/0008677 A1 * | 1/2005 | Modliszewski ........ A61Q 19/00 424/439 |
| 2005/0019374 A1 * | 1/2005 | Modliszewski .......... A61K 8/73 424/439 |
| 2019/0211189 A1 * | 7/2019 | Worm ................... A61K 9/4816 |
| 2019/0254979 A1 * | 8/2019 | Kim ...................... A61K 9/4816 |
| 2019/0269623 A1 * | 9/2019 | Bayless ................ A61K 9/4816 |

FOREIGN PATENT DOCUMENTS

| CN | 102670563 A | 9/2012 |
| CN | 103893771 A | 7/2014 |
| CN | 104721167 A | 6/2015 |
| CN | 105434397 A | 3/2016 |
| CN | 107072958 A | 8/2017 |
| WO | 0191721 A2 | 12/2001 |

OTHER PUBLICATIONS

Li et al., Carrageenan and its applications in drug delivery. Carbohydrate Polymers 103 (2014) 1- 11. (Year: 2014).*
Fu et al. Effect of Molar Substitution on the Properties of Hydroxypropyl Starch. Molecules 2022, 27, 2119. (Year: 2022).*

* cited by examiner

*Primary Examiner* — Robert A Wax
*Assistant Examiner* — Olga V. Tcherkasskaya
(74) *Attorney, Agent, or Firm* — SZDC Law P.C.

(57) ABSTRACT

The present disclosure belongs to the technical field of soft capsules, and particularly relates to a plant soft capsule and a preparation method and application thereof. The plant soft capsule with excellent performance is prepared from carrageenan, starch, a plasticizer and water by controlling the weight-average molecular weight of the carrageenan to be $1.2 \times 10^6$ to $2.0 \times 10^6$. Compared with a plant soft capsule in the existing technology, the plant soft capsule of the present discourse has lower production cost, and the product quality meets the requirements of gelatin soft capsules; and on the premise of high production efficiency, a low oil leakage rate is achieved, and the rupture time meets United States Pharmacopoeia (USP) standards. The plant soft capsule prepared according to the present disclosure can be filled with an active component as a content and used for preparation of a plurality of drugs, functional food or dietary nutritional supplements.

1 Claim, 3 Drawing Sheets

PLANT SOFT CAPSULE AND PREPARATION METHOD AND APPLICATION THEREOF

This application is the National Stage Application of PCT/CN2019/091929, filed on Jun. 19, 2019, which claims priority to Chinese Patent Application No. 2019105088399, filed on Jun. 12, 2019, which is incorporated by reference for all purposes as if fully set forth herein.

TECHNICAL FIELD

The present disclosure belongs to the technical field of soft capsules, and more particularly relates to a plant soft capsule and a preparation method and application thereof.

BACKGROUND ART

Soft capsules are widely used in the fields of medical treatment and medicine products thereof and food. Gelatin is used as a main raw material for gelatin skins of commonly-used soft capsule products at present, the gelatin is mainly derived from collagen parts in connective tissue such as animal skins, bones and sarcolemma, and the gelatin commonly used in the food industry is mostly derived from pigs and cattle. In recent years, many edible safety incidents of capsules have been reported, because industrial gelatin contains more heavy metal ions, the harm is great; and the gelatin is low in cost, but has the problem of crosslinking, so that the soft capsules easily become unstable, and the storage and transportation of soft capsule products are influenced. Meanwhile, due to the animal origin of the gelatin, the soft capsules taking the gelatin as the main component also do not meet dietary habits and requirements of the Muslim or vegetarianism. Based on the above reasons, the development of plant soft capsules has important significance.

At present, there are a large number of patent literature reports on the related topics of plant soft capsules. For example, in CN 103893771 B, hydroxypropyl starch is used as a main raw material and added with an auxiliary material consisting of a gel, a softening agent and a film-forming agent and capable of improving the properties of the soft capsules, as well as an opacifying agent, a coloring agent and a flavoring agent which can change the appearance and odor of the soft capsules, and the like, so as to prepare starch-based gum skins. The defects are that compared with other gum raw materials, the gum skins mainly prepared from the hydroxypropyl starch are more brittle, the elasticity and toughness of the gum skins are poor, and the crushing possibility of finally finished pills is higher; and in addition, one or more of calcium chloride, potassium chloride, potassium citrate and other ions must be added in the preparation process.

In CN 102670563 A, pullulan polysaccharide is used as a main raw material and mixed with a plurality of biological polysaccharides or seaweed polysaccharides to form a film through a plurality of procedures and be rolled into pills by adopting a soft capsule machine through a rotary film method, and the characteristic is that the prepared soft capsule pills can reach a level similar to that of gelatin capsules in the aspects of transparency, elasticity, mechanical strength and the like and are completely disintegrated in a relevant specified time. The defects are that the pullulan polysaccharide is high in price and cost and has no possibility of replacing gelatin soft capsules; and moreover, the drying time after a gum solution forms the film is long, the film needs to be dried for 10 to 18 h at 60 to 70° C., and the production efficiency is low.

In order to reduce the cost of the pullulan polysaccharide in the scheme of CN 102670563 A, in CN 105434397 B, hydroxypropyl starch and hydroxypropyl methyl cellulose are adopted to replace part of the pullulan polysaccharide. Part of production cost can be reduced in the patent, and gum skins of prepared soft capsules have low brittleness, excellent disintegration performance and no difference with gelatin soft capsules. Moreover, a gum skin composition does not need to be subjected to film spreading and drying in advance, and after a prepared gum solution reaches the controlled viscosity, the gum solution can be directly connected with gum feeding equipment of a pill rolling machine to directly perform pill rolling to prepare the soft capsules, so that the production efficiency is improved. However, all of the hydroxypropyl starch, the hydroxypropyl methyl cellulose and the pullulan polysaccharide in this patent are indispensible, otherwise the brittleness and disintegration time of the soft capsules would be affected (see Embodiments 9 to 14 in Table 2 on page 9 of the description in CN 105434397 B); in addition, the addition amounts of the hydroxypropyl starch, the hydroxypropyl methyl cellulose and the pullulan polysaccharide must be strictly controlled, the addition amount of the pullulan polysaccharide must meet certain conditions, and the insufficient addition amount can lead to embrittlement and particle breakage. Therefore, although the hydroxypropyl starch and the hydroxypropyl methyl cellulose are adopted to replace part of the pullulan polysaccharide to a certain extent and part of production cost is reduced, the use of the pullulan polysaccharide cannot be fundamentally avoided to reduce the production cost; and in addition, calcium chloride, potassium chloride, potassium citrate and other ions are also used in this patent to achieve excellent film-forming property so as to achieve certain gum skin toughness.

In CN 104721167 A, a combination of common starch and modified starch is used as a starch matrix, and a plasticizer, a gel and deionized water are added to prepare starch soft capsules. The prepared soft capsules have the advantages of high transparency, good toughness, shortened disintegration time and the like. However, since a preparation technology adopted in the preparation process is a conventional preparation method, film spreading and drying are needed in advance, and film spreading and drying time is often long.

In summary, the plant soft capsules reported in the existing technology have the defects of high raw material cost, long gum skin drying time in the preparation process, low production efficiency, poor encapsulation property, additional addition of metal ions to ensure film forming property and the like, the two key factors of cost and quality in the plant soft capsules cannot be solved simultaneously, and the degree that the plant soft capsules industrially replace the gelatin soft capsules cannot be achieved.

SUMMARY OF THE INVENTION

The present disclosure aims to solve the problems that low cost and high quality cannot be simultaneously met in existing plant soft capsule technologies, and provides a plant soft capsule with industrial application and a preparation method thereof. The plant soft capsule with excellent performance is prepared from carrageenan, starch, a plasticizer and water by controlling the weight-average molecular weight of the carrageenan. Compared with plant soft capsules in the existing technology, the plant soft capsule of the present disclosure has lower production cost, and the product quality meets the requirements of gelatin soft capsules.

On the premise of high production efficiency, a low oil leakage rate can be achieved and the rupture time meets United States Pharmacopeia (USP) standards.

According to a first aspect of the present disclosure, the present disclosure provides a plant soft capsule including carrageenan, starch, a plasticizer and water, and the weight-average molecular weight Mw of the carrageenan is $1.20 \times 10^6$ to $2.00 \times 10^6$. The weight-average molecular weight Mw of conventional carrageenan is $2.0 \times 10^5$ or above, and in the research process, the applicant finds that when a proportion of the carrageenan with small molecular weight distribution is too high, a prepared gum solution is too viscous and has no good film forming property, and when the proportion of the carrageenan with small molecular weight distribution is too low, a prepared gum solution has insufficient viscosity; however, when a proportion of the carrageenan with high molecular weight distribution is too high, a gum solution has strong water absorbability and no toughness, and when the proportion of the carrageenan with the high molecular weight distribution is too low, the gum solution has no film forming property; and plant soft capsules meeting the requirements cannot be prepared when the proportion is too high or too low. The applicant surprisingly finds that a gum solution prepared with the carrageenan with the limited weight-average molecular weight range of the present disclosure as a gel has excellent flowability and film forming property, and on the premise of removing metal ion additives such as calcium chloride, potassium chloride or potassium citrate, the prepared plant soft capsule can meet the requirements of soft capsule film forming property and gum skin toughness, and the rupture time is remarkably shortened to meet the requirements of the USP standards.

Preferably, the plant soft capsule includes, in parts by weight, 3 to 20 parts of the carrageenan, 10 to 50 parts of the starch, 10 to 35 parts of the plasticizer and 30 to 70 parts of the water; and on the premise of limiting the weight-average molecular weight of the carrageenan, the person skilled in the art can adjust the proportion of the plant soft capsule of the present disclosure according to the properties of products in combination with known techniques.

Preferably, the carrageenan is one or any combination of two or more of a K type (Kappa), an I type (Iota) and an L type (Lambda), and the carrageenan further preferably is the I type (Iota) or a combination of the I type (Iota) and the K type (Kappa). In the combination of the I type and the K type, the I type: the K type is calculated to be 9.9:0.1 to 7.0:3.0 according to weight ratio, e.g. the I type: the K type=8:1. An experiment shows that the film forming property of a gum solution prepared from L-type carrageenan is poor, and a gum solution prepared from pure K-type carrageenan is better in film forming property, but poor in viscosity. A gum solution prepared from pure I-type carrageenan or I-type+K-type carrageenan is easily spread to form a film and is moderate in viscosity, a gum skin is good in toughness and difficult to break, an oil leakage rate of produced capsules is low, and production efficiency is high.

Preferably, the plasticizer is one or any combination of two or more of glycerin, sorbitol, xylitol and polyethylene glycol, and further preferably is the glycerin.

Preferably, the starch is modified starch, and the modified starch is one or a combination of two or more of oxidized starch, acidic starch, hydroxypropyl starch and oxidized hydroxypropyl starch in any weight ratio, and further preferably is the hydroxypropyl starch or the oxidized hydroxypropyl starch.

Preferably, the plant soft capsule further includes a pigment, an opacifying agent or a flavoring agent. The pigment is a natural pigment and a synthetic pigment. The natural pigment is brown (caramel), blue (*spirulina* blue), or purple red (purple sweet potato red) or orange (annatto), and the synthetic pigment is one or more of carmine, lemon yellow, sunset yellow, indigo and the like. Compared with the synthetic pigment, the natural pigment is more green and safer, but because the temperature of a production process of the plant soft capsule is high, the natural pigment are very easy to fade at high temperature. According to the present disclosure, the influence of various pigments on the performance of the gum solution is tested, and it is found that when an addition proportion of the caramel is high, the viscosity of the gum solution is very strong, but the performance of the gum solution is poor, and the gum solution cannot be spread to form a film. The purple sweet potato red can meet production requirements, but this natural pigment is very easy to fade at high temperature. Although red iron oxide does not fade at high temperature, the gum solution has poor performance. After screening for many times, it is found that annatto and *spirulina* blue pigments do not affect the performance of the gum solution, and do not fade at high temperature for a certain time, which is of great significance for enriching product types. In order to enrich the colors of soft capsules and solve the problem of fading of the purple sweet potato red, different kinds of color fixatives are researched, finally meglumine is screened out to serve as the color fixative, and prepared soft capsules do not fade in long-term storage at high temperature and have practical industrial application prospects.

According to one aspect of the present disclosure, the present disclosure provides a preparation method of a plant soft capsule, and the preparation method includes the following steps:

1) Gum Dissolving Process weighing carrageenan, starch, a plasticizer and water in a formula amount, heating until a gum solution swells, preserving heat, and degassing until the gum solution is clear and transparent to obtain the gum solution; and 2) Pill Rolling Process heating a gum box of a pill rolling machine, heating a rotary drum, supplying gum, setting a thickness of a gum skin, rolling pills after setting a machine speed of the pill rolling machine, drying until the gum pills reach a certain hardness, selecting the pills, and finally packaging the pills, wherein the certain hardness is the hardness between 50 N and 70 N.

Preferably, the heating temperature in step 1) is 80 to 90° C., and the heat preservation time is 20 to 120 min.

Preferably, the thickness of the gum skin in step 2) is less than 1.0 mm, and further preferably is 0.30 mm to 0.60 mm. At present, the hardness of the capsule is ensured and the oil leakage rate of the plant soft capsule is controlled by increasing the thickness (0.70 mm to 0.90 mm) of the gum skin of the soft capsule and sacrificing the rotating speed (1.5 rpm) of the pill rolling machine in the industry. According to the present disclosure, on the basis of controlling the thickness of the gum skin to be 0.30 mm to 0.60 mm, high rotating speed and low oil leakage rate are achieved. The plant soft capsule process of the present disclosure can reduce the thickness of the gum skin to half of the normal level or even lower, and can also ensure the hardness and the extremely low oil leakage rate (less than 1%) of the capsule, which has extremely great significance for controlling the cost of the soft capsule.

Preferably, the temperature for heating the gum box of the pill rolling machine in the step 2) is 80 to 95° C.; and the heating temperature of the rotary drum is 20 to 40° C. At present, rotary drums of pill rolling machines in the industry are all refrigerated, and the purpose of refrigerating is to enable a gelatin solution to be cooled and formed as soon as possible; and although the purpose of cooling and forming as soon as possible can be achieved by adopting refrigerating, a plant gum solution of the present disclosure is high in moisture content, is difficult to dry to form a gum skin with good toughness by the refrigerating method, so that the content loading capacity is small, and the oil leakage rate is high. According to the present disclosure, the rotary drum is heated, the plant gum skin passing the heated rotary drum can be quickly dried, and has good toughness and viscosity, the early drying time is saved, the gum skin quality is guaranteed, the machine speed is increased, and the production efficiency is guaranteed.

According to another aspect of the present disclosure, the present disclosure provides application of a plant soft capsule. The plant soft capsule is filled with an active component as a content and used for preparation of drugs, functional food or dietary nutritional supplements.

The drugs, the functional food or the dietary nutritional supplements are Danqi soft capsules, linseed oil plant soft capsules, vitamin E plant soft capsules, evening primrose seed oil plant soft capsules, biotin plant soft capsules, lutein plant soft capsules, coenzyme Q10 plant soft capsules, vitamin K2 plant soft capsules, phospholipid plant soft capsules, conjugated linoleic acid plant soft capsules, coconut oil plant soft capsules, multivitamin mineral plant soft capsules, DHA algal oil plant soft capsules and fish oil plant soft capsules.

The linseed oil plant soft capsules are prepared by taking linseed oil as a content, and carrageenan, hydroxypropyl starch, glycerin and water as main gum skin components. The linseed oil contains high levels of α-linolenic acid, and the α-linolenic acid has the effects of resisting tumors, resisting thrombus, reducing blood fat, nourishing brain cells, regulating plant nerves and the like.

The vitamin E plant soft capsules are prepared by taking vitamin E and soybean oil as contents, and carrageenan, hydroxypropyl starch, glycerin and water as main gum skin components. The vitamin E is a fat-soluble vitamin, a hydrolysate of the vitamin E is tocopherol, which is one of main antioxidants.

The evening primrose seed oil plant soft capsules are prepared by taking evening primrose seed oil as a content, and carrageenan, hydroxypropyl starch, glycerin and water as main gum skin components. The evening primrose seed oil has the effects of preventing cardiovascular diseases, premenstrual syndrome, climacteric syndrome and the like.

The biotin plant soft capsules are prepared by taking biotin, rice bran oil, phospholipid and beeswax as contents, and carrageenan, hydroxypropyl starch, glycerin and water as main gum skin components. The biotin is a necessary nutrient for maintaining human body natural growth and development and normal human body function health, not only has an effect of preventing hair loss and balding, but also can prevent juvenile canities common in modern people.

Vitamin D3 plant soft capsules are prepared by taking vitamin D3 and rice bran oil as contents, and carrageenan, hydroxypropyl starch, glycerin and water as main gum skin components. The vitamin D3 can promote the absorption of calcium and phosphorus by organisms, so that levels of plasma calcium and plasma phosphorus reach a saturation degree, growth and bone calcification are promoted, and tooth perfection is promoted.

The lutein plant soft capsules are prepared by taking lutein, rice bran oil, beeswax and phospholipid as contents, and carrageenan, hydroxypropyl starch, glycerin and water as main gum skin components. The natural lutein is an excellent antioxidant and can prevent free radicals from causing cell and organ damage in human bodies, and accordingly preventing cardiovascular sclerosis, coronary heart diseases, tumor diseases and the like caused by aging of the body.

The coenzyme Q10 plant soft capsules are prepared by taking coenzyme Q10, rice bran oil, beeswax and phospholipid as contents and carrageenan, hydroxypropyl starch, glycerin and water as main gum skin components. The coenzyme Q10 not only can provide power for the heart, but also has excellent antioxidation and free radical scavenging functions, can prevent lipid peroxidation of blood vessel walls and atherosclerosis, and has no toxic or side effect.

The vitamin K2 plant soft capsules are prepared by taking vitamin K2 and rice bran oil as contents and carrageenan, hydroxypropyl starch, glycerin and water as main gum skin components. The vitamin K2 is a fat-soluble vitamin, a derivative of a naphthoquinone group with plastoquinone biological activity, and one of indispensable important vitamins in human bodies, and can treat and prevent osteoporosis.

The phospholipid plant soft capsules are prepared by taking phospholipid as a content and carrageenan, hydroxypropyl starch, glycerin and water as main gum skin components. The phospholipid can decompose excessive blood fats and excessive cholesterol, clean blood vessels and make the circulation of blood vessels smooth, and is recognized as a blood vessel scavenger.

The conjugated linoleic acid plant soft capsules are prepared by taking conjugated linoleic acid as a content and carrageenan, hydroxypropyl starch, glycerin and water as main gum skin components. The conjugated linoleic acid has multiple important physiological functions of resisting tumors, resisting oxidation, resisting atherosclerosis, improving immunity, improving bone density, preventing diabetes and the like, and can further reduce cholesterol of animals and human bodies, triglyceride and low-density lipoprotein cholesterol, also can reduce fats of animals and human bodies, and increase muscles.

The coconut oil plant soft capsules are prepared by taking coconut oil as a content and carrageenan, hydroxypropyl starch, glycerin and water as main gum skin components. The coconut oil is the only grease consisting of a medium-chain fatty acid in daily food and thus can improve the metabolic efficiency.

The multivitamin mineral plant soft capsules are prepared by taking vitamins such as vitamin A, vitamin $B_2$, vitamin $B_6$, vitamin $B_{12}$, vitamin C, vitamin $D_3$ and vitamin E and minerals such as calcium, iron, zinc and selenium as main active components, adding soybean oil, phospholipid and beeswax to prepare contents, and taking carrageenan, hydroxypropyl starch, glycerin and water as main gum skin components, so as to supplement various vitamins and minerals required by human bodies.

The DHA algal oil plant soft capsules are prepared by taking DHA algal oil as a content and carrageenan, hydroxypropyl starch, glycerin and water as main gum skin components. DHA is a main element for growth and maintenance of nervous system cells and is an important constituent fatty acid of brain and retinas, the content of DHA in cerebral cortex of a human body is up to 20%, the proportion of DHA in retinas of eyes is the largest and accounts for about 50%, and DHA is essential for the development of intelligence and vision of infants.

The fish oil plant soft capsules are prepared by taking fish oil as a content and carrageenan, hydroxypropyl starch, glycerin and water as main gum skin components. The fish oil is a fat extracted from greasy fish, is rich in ω-3 polyunsaturated fatty acids (DHA and EPA), and has the healthy benefits of resisting inflammation, adjusting blood lipids and the like.

According to the present disclosure, when the plant soft capsule is researched, it is surprisingly found that when the molecular weight of the carrageenan is limited to a certain range, a gum solution composed of the carrageenan, the hydroxypropyl starch, the plasticizer and the water has good film forming property, and the present disclosure has the following beneficial effects compared with the existing technology.

1) The plant soft capsule of the present disclosure is simple in raw material, only the starch, the plasticizer and the water are required to be added on the premise of controlling the molecular weight of the carrageenan, expensive pullulan polysaccharide is not required to be added, and the production cost of the plant soft capsule is reduced to a great extent.

2) On the premise that soluble salts such as calcium chloride, potassium chloride and potassium citrate are removed as film-forming agents, the prepared plant soft capsule can realize excellent film forming property, the gum skin toughness is higher, and the rupture time is greatly shortened.

3) According to the present disclosure, by optimizing the carrageenan type, the molecular weight and the starch type, high pill rolling speed and low oil leakage rate of the plant soft capsule can be realized on the basis of controlling the thickness of the gum skin to be 0.30 mm to 0.60 mm; and the low oil leakage rate is guaranteed without sacrificing production efficiency or increasing the gum skin thickness.

4) The thickness of the gum skin of the plant soft capsule prepared in the present disclosure is far lower than half of the normal level or even lower, and the hardness and extremely low oil leakage rate of the capsule can be guaranteed, which has extremely great significance for controlling the cost of the soft capsule.

5) Compared with other pure starch plant gums, the production efficiency is greatly improved, pure starch gum skins are insufficient in toughness and high in oil leakage rate, the machine speed is greatly limited and is only 1.5 rpm, and the plant soft capsule of the present disclosure can be completely compared with gelatin by being produced at the machine speed of 1.5 rpm to 5.0 rpm; and moreover, the drying time after capsule forming is greatly shortened, and the coexisting problem that the drying time of many plant soft capsules is too long is solved.

6) The viscosity of starch and carrageenan is too large, and the rupture time of plant soft capsules is generally about 30 minutes; and according to the present disclosure, by removing the film-forming agents of the soluble salts and reducing the thickness of the gum skin, the rupture time of the soft capsule can be made to be less than 15 minutes, which meets the USP standards.

7) For ordinary gelatin soft capsules, due to limitation of gelatin raw materials, gelatin is dissolved when the temperature is too high, the dissolved gelatin has viscosity, such that the soft capsules adhere to each other, so that the conventional gelatin soft capsules require cold-storage; the plant soft capsule prepared in the present disclosure perfectly solves this problem, and the gum skin of the plant soft capsule prepared by the present disclosure has resistance to high temperature and can still be insoluble and non-sticky even in high-temperature weather in summer; and the requirements for logistics transportation and storage conditions are low, and a large amount of cost is saved.

Glossary explanation: Mn represents number-average molecular weight, Mw represents weight-average molecular weight, Mz represents average molecular weight, and Mw/Mn represents polydispersity index.

BRIEF DESCRIPTION OF THE DRAWINGS

In FIGS. 1-3, the horizontal axis represents a logarithm of the molecular weight; and the vertical axis represents that a vertical axis value of a point on the curve is a numerical value related to content of sample molecules at each molecular weight

DETAILED DESCRIPTION OF THE INVENTION

Figure 1:
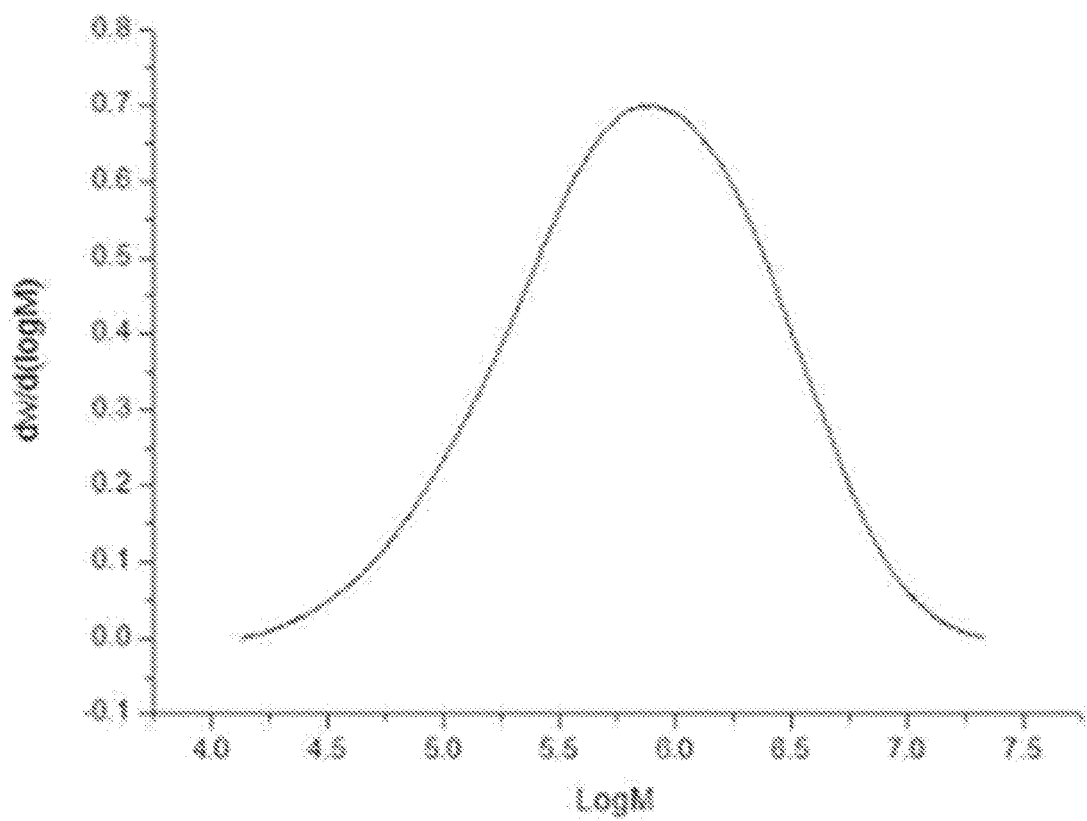
FIG. 1 is a detection diagram of typical commercial carrageenan with high molecular weight, wherein the weight-average molecular weight Mw=$2.40 \times 10^6$.
Figure 2:
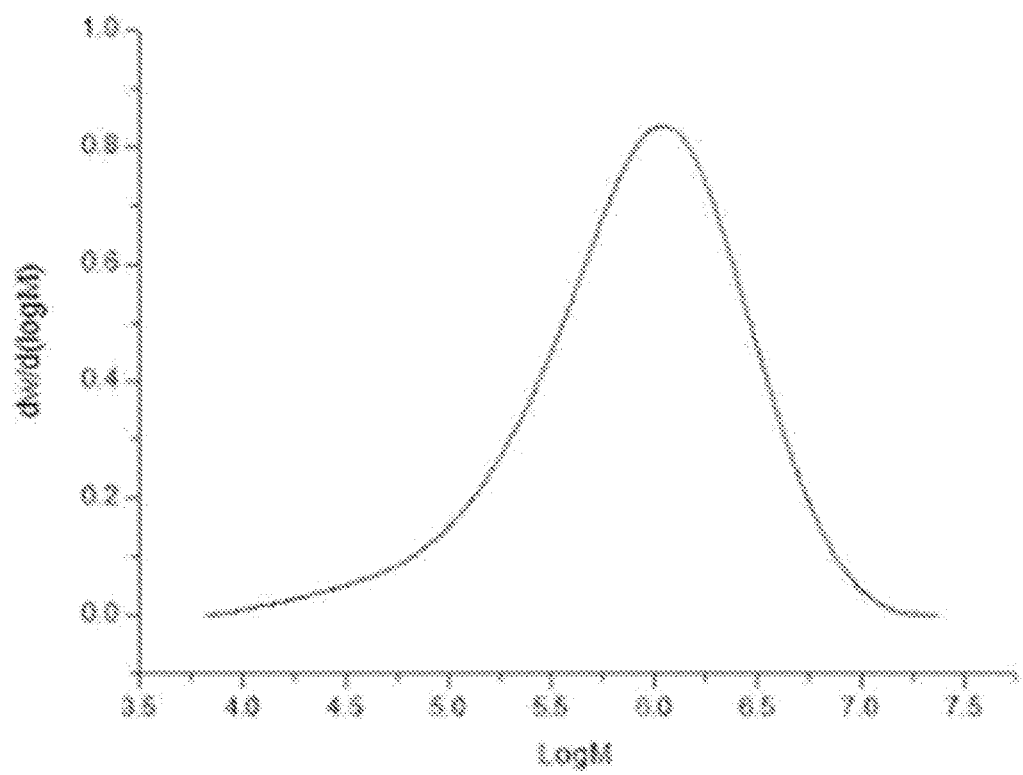
FIG. 2 is a detection diagram of typical commercial carrageenan with low molecular weight, wherein the weight-average molecular weight Mw=$1.12 \times 10^6$.
Figure 3:
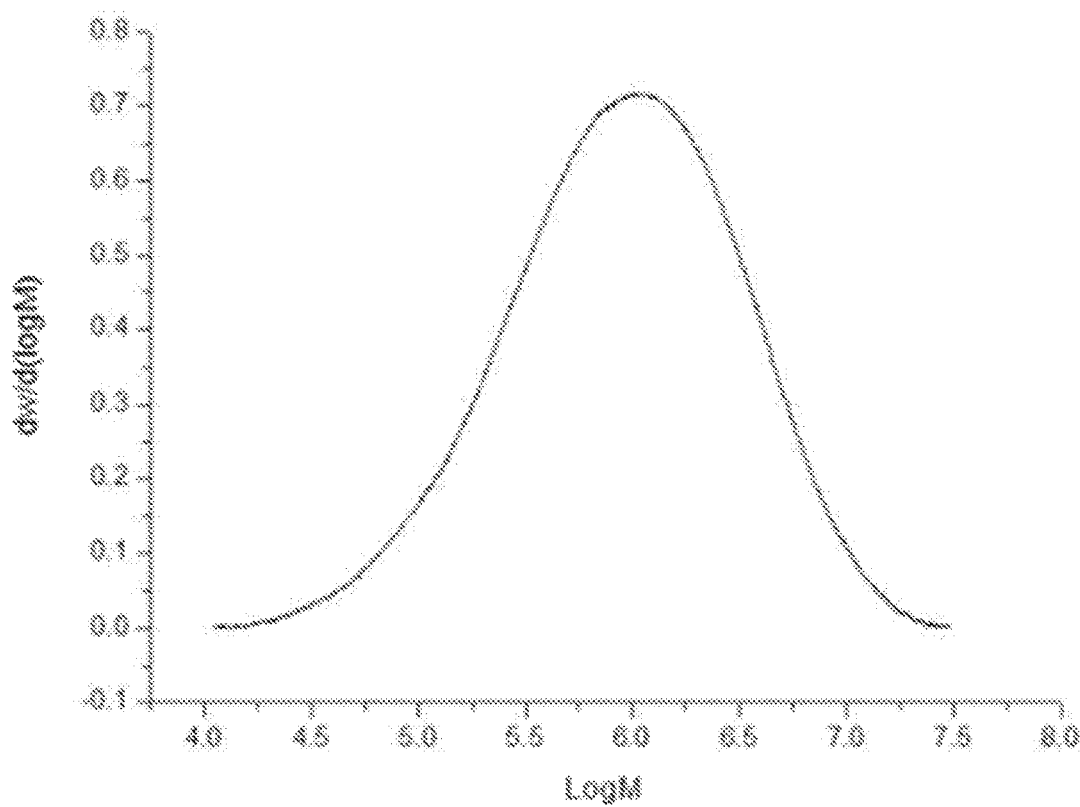
FIG. 3 is a detection diagram of typical carrageenan with limited molecular weight according to the present disclosure, wherein the weight-average molecular weight Mw=$1.78 \times 10^6$.

For the purpose of making objectives, technical schemes and advantages of the present disclosure clearer, further detailed description will be made to the present disclosure in conjunction with specific embodiments. It should be understood that these descriptions are exemplary only and are not intended to limit the scope of the present disclosure.

Devices involved in embodiments: gum dissolving tank TRRJ-10, from Wenzhou Tianrui Pharmaceutical Machinery Co., Ltd.; full-automatic soft capsule machine BCM-GB6, from BOCHANG Co., Ltd.; and SLX-A hardness tester, from Wenzhou Shandu Instrument Co., Ltd.

Main Detection Indexes of Soft Capsules:
1) gum skin joint rate: a ratio of the joint thickness of gum skins to the thickness of the gum skins; 2) oil leakage rate: a ratio of soft capsules leaking oil to all soft capsules; 3) content loading capacity: the maximum loading capacity of a mold; 4) rupture time: referring to a rupture experiment in USP <2040>; and 5) hardness: the hardness of dried soft capsules, for measurement of the drying effect of the soft capsules.

Embodiment 1

Influence of Different Types of Carrageenan on Prepared Soft Capsules
1) Gum Dissolving Process
8 KG of different types of carrageenan, 30 KG of hydroxypropyl starch, 15 KG of glycerin and 47 KG of purified water were weighed, put in a gum dissolving tank and heated to 80 to 90° C. to enable a gum solution to swell, then heat was preserved for 20 to 120 min, and degassing was performed until the gum solution was clear and transparent to obtain the gum solution.
2) Pill Rolling Process
A 22-minim cylindrical soft capsule mold was selected, a gum box of a pill rolling machine was heated to 80 to 95°

C., a rotary drum was heated to 20 to 40° C., gum was supplied, the thickness of gum skins was set to be 0.80 mm, pill rolling was performed at a machine speed of 1.5 rpm, the content was linseed oil, pills were dried until the hardness of the gum pills met the requirement (50 to 70 N), and the pills were selected and finally packaged.

The gum skin joint rate, the content loading capacity and the oil leakage rate of soft capsules prepared from the different types of carrageenan were detected, and the result is shown in Table 1.

TABLE 1

Influence of Types of Carrageenan on Products

| Carrageenan | I type | K type | L type | I type + K type |
|---|---|---|---|---|
| Gum skin joint rate | 70% | 0% | 0% | 75% |
| Content loading capacity | 800 mg | 0 | 0 | 850 mg |
| Oil leakage rate | Less than 1% | 100% | 100% | Less than 1% |

Note: in Table 1, the weight-average molecular weight of I-type carrageenan is $1.2 \times 10^6$, the weight-average molecular weight of K-type carrageenan is $2.0 \times 10^6$, and the weight-average molecular weight of L-type carrageenan is $1.8 \times 10^6$; and I type+K type means that the I-type carrageenan and the K-type carrageenan are used as raw materials, and the weight ratio of the I type: the K type is calculated and may be in the range of 9.9:0.1 to 7.0:3.0, and is 8:1 in the present embodiment.

It is found in the experiment that the gum solution prepared from the L-type carrageenan has no gelation performance and cannot be spread to form a film, and the gum solution prepared from the pure K-type carrageenan has good film forming property but poor viscosity. Only the gum solution prepared from the pure I-type or I-type+K-type carrageenan is easy to spread to form a film and moderate in viscosity, the gum skins are good in toughness and not easy to break, the oil leakage rate of the produced capsules is low, and the production efficiency is high.

Embodiment 2

Influence of Carrageenan With Different Weight-Average Molecular Weights on Prepared Soft Capsules 1) Gum Dissolving Process 8 KG of I-type (Iota) carrageenan with different weight-average molecular weights, 30 KG of hydroxypropyl starch, 15 KG of glycerin and 47 KG of purified water were weighed, put in a gum dissolving tank and heated to 80 to 90° C. to enable a gum solution to swell, then heat was preserved for 20 to 120 min, and degassing was performed until the gum solution was clear and transparent to obtain the gum solution.

2) Pill Rolling Process

A 22-minim cylindrical soft capsule mold was selected, a gum box of a pill rolling machine was heated to 80 to 95° C., a rotary drum was heated to 20 to 40° C., gum was supplied, the thickness of gum skins was set to be 0.80 mm, pill rolling was performed at a machine speed of 1.5 rpm, the content was linseed oil, pills were dried until the hardness of the gum pills met the requirement (50 to 70 N), and the pills were selected and finally packaged.

The gum skin joint rate, the content loading capacity and the oil leakage rate of soft capsules prepared from the carrageenan with different weight-average molecular weights were detected, and the result is shown in Table 2.

TABLE 2

Influence of Weight-average Molecular Weights of Carrageenan on Products

| Carrageenan Mw | $1.0 \times 10^6$ | $1.2 \times 10^6$ | $1.5 \times 10^6$ | $2.0 \times 10^6$ | $2.5 \times 10^6$ |
|---|---|---|---|---|---|
| Gum skin joint rate | 40% | 60% | 70% | 50% | 20% |
| Content loading capacity | 600 mg | 800 mg | 850 mg | 800 mg | 400 mg |
| Oil leakage rate | 20% | Less than 1% | Less than 1% | Less than 1% | 50% |

It is found in the experiment that when the proportion of carrageenan with small molecular weight is too high, the viscosity of the gum skins is strong, but the film forming property is poor, resulting in low loading capacity and high oil leakage rate. When the proportion of carrageenan with high molecular weight is too high, the film forming property of the gum solution is good, and the gum solution can be uniformly spread on the surface of the rotary drum, but the viscosity of the gum skins is poor, the joint rate is low, and the oil leakage of the rolled pills is obvious. Only when the weight-average molecular weight of the carrageenan is stable between $1.20 \times 10^6$ and $2.00 \times 10^6$, the gum solution is easy to spread to form a film and moderate in viscosity, the gum skins are good in toughness and not easy to break, and the production efficiency is high.

Embodiment 3

Influence of Different Rotary Drum Temperatures on Properties of Prepared Soft Capsules 1) Gum Dissolving Process 8 KG of I-type (Iota) carrageenan (the weight-average molecular weight of the carrageenan is $1.50 \pm 0.1 \times 10^6$), 30 KG of hydroxypropyl starch, 15 KG of glycerin and 47 KG of purified water were weighed, put in a gum dissolving tank and heated to 80 to 90° C. to enable a gum solution to swell, then heat was preserved for 20 to 120 min, and degassing was performed until the gum solution was clear and transparent to obtain the gum solution.

2) Pill Rolling Process

A 22-minim cylindrical soft capsule mold was selected, a gum box of a pill rolling machine was heated to 80 to 95° C., a rotary drum was heated, gum was supplied, the thickness of gum skins was set to be 0.80 mm, pill rolling was performed at a machine speed of 1.5 rpm, the content was linseed oil, pills were dried until the hardness of the gum pills met the requirement (50 to 70 N), and the pills were selected and finally packaged.

The gum skin joint rate, the content loading capacity and the oil leakage rate of soft capsules prepared at different rotary drum temperatures were detected, and the result is shown in Table 3.

TABLE 3

| Influence of Different Rotary Drum Temperatures on Products | | | | | |
| --- | --- | --- | --- | --- | --- |
| Rotary drum temperature | 15° C. | 20° C. | 30° C. | 40° C. | 50° C. |
| Gum skin joint rate | 50% | 60% | 70% | 70% | 40% |
| Content loading capacity | 600 mg | 800 mg | 850 mg | 850 mg | 700 mg |
| Oil leakage rate | 20% | Less than 1% | Less than 1% | Less than 1% | 40% |

Different rotary drum temperatures have a great influence on the toughness of the gum skins, and at present, rotary drums of pill rolling machines in the industry are all refrigerated, so that a gelatin solution is cooled and formed as soon as possible, but the moisture content of the plant gum solution of the present disclosure is high and is difficult to dry quickly by a conventional refrigeration method to form gum skins with good toughness. The rotary drum is heated, the plant gum skins which pass the rotary drum with the heating function can be dried quickly, the toughness and the viscosity are good, and the early drying time is saved. Through the experiment, it is found that when the rotary drum temperature is low, the gum skins are dried slowly and the toughness is not enough, resulting in lower loading capacity and high oil leakage rate. When the rotary drum temperature is high, the water loss of the gum skins is too fast, so that the viscosity of the gum skins is reduced, the joint rate is low, and finally oil leakage is caused. Thus the preferred rotary drum temperature range is 20 to 40° C.

Embodiment 4

Influence of Different Plasticizers on Properties of Prepared Soft Capsules

1) Gum Dissolving Process

8 KG of I-type (Iota) carrageenan (the weight-average molecular weight of the carrageenan was $1.50\pm0.1\times10^6$), 30 KG of hydroxypropyl starch, 15 KG of a plasticizer and 47 KG of purified water were weighed, put in a gum dissolving tank and heated to 80 to 90° C. to enable a gum solution to swell, then heat was preserved for 20 to 120 min, and degassing was performed until the gum solution was clear and transparent to obtain the gum solution.

2) Pill Rolling Process

A 22-minim cylindrical soft capsule mold was selected, a gum box of a pill rolling machine was heated to 80 to 95° C., a rotary drum was heated to 20 to 40° C., gum was supplied, the thickness of gum skins was set to be 0.80 mm, pill rolling was performed at a machine speed of 1.5 rpm, the content was linseed oil, pills were dried until the hardness of the gum pills met the requirement (50 to 70 N), and the pills were selected and finally packaged.

The gum skin joint rate, the content loading capacity and the oil leakage rate of soft capsules prepared from different plasticizers were detected, and the result is shown in Table 4.

TABLE 4

| Influence of Different Plasticizers on Products | | | | |
| --- | --- | --- | --- | --- |
| Plasticizer | Glycerin | Sorbitol | Xylitol | Polyethylene glycol |
| Gum skin joint rate | 70% | 60% | 40% | 30% |
| Content loading capacity | 850 mg | 700 mg | 500 mg | 400 mg |
| Oil leakage rate | Less than 1% | Less than 1% | 20% | 40% |

The plasticizers have a great influence on the toughness of the gum skins, the toughness of the gum skins determines the loading capacity range of capsules, and the better the toughness is, the larger the loading capacity is. Glycerin, sorbitol, xylitol and polyethylene glycol were tested as plasticizers, and it is found that glycerin gum skins have the best toughness, the loading capacity of the capsules can be up to 850 mg, when the sorbitol, the xylitol or the polyethylene glycol is used as the plasticizer for the same mold, the gum skin toughness is insufficient, the loading capacity of the capsules is low, and when the xylitol and the polyethylene glycol are used as plasticizers, the oil leakage rate is high, so the glycerin is preferred as the gum skin plasticizer.

Embodiment 5

Influence of Different Starch Types on Properties of Prepared Soft Capsules

1) Gum Dissolving Process

8 KG of I-type (Iota) carrageenan (the weight-average molecular weight of the carrageenan was $1.50\pm0.1\times10^6$), 30 KG of starch, 15 KG of glycerin and 47 KG of purified water were weighed, put in a gum dissolving tank and heated to 80 to 90° C. to enable a gum solution to swell, then heat was preserved for 20 to 120 min, and degassing was performed until the gum solution was clear and transparent to obtain the gum solution.

2) Pill Rolling Process

A 22-minim cylindrical soft capsule mold was selected, a gum box of a pill rolling machine was heated to 80 to 95° C., a rotary drum was heated to 20 to 40° C., gum was supplied, the thickness of gum skins was set to be 0.80 mm, pill rolling was performed at a machine speed of 1.5 rpm, the content was linseed oil, pills were dried until the hardness of the gum pills met the requirement (50 to 70 N), and the pills were selected and finally packaged.

The gum skin joint rate, the content loading capacity and the oil leakage rate of soft capsules prepared from different types of starch were detected, and the result is shown in Table 5.

TABLE 5

| Influence of Different Starch on Products | | | | |
| --- | --- | --- | --- | --- |
| Starch | Oxidized starch | Acidic starch | Hydroxypropyl starch | Oxidized hydroxypropyl starch |
| Gum skin joint rate | 10% | 20% | 70% | 70% |
| Content loading capacity | 300 mg | 500 mg | 850 mg | 900 mg |
| Oil leakage rate | 80% | 60% | Less than 1% | Less than 1% |

The starch has a great influence on the viscosity of the gum skins, when the viscosity of the gum skins is too low, the joint thickness is insufficient and the oil leakage rate is high, and when the viscosity of the gum skins is too high, the gum skins is easy to adhere to the surface of the rotary drum, and the production efficiency is influenced. Therefore, oxidized starch, acidic starch, hydroxypropyl starch and oxidized hydroxypropyl starch were screened and tested respectively, it is found that the viscosity of gum skins prepared from the oxidized starch and the acidic starch is insufficient, and the prepared capsules is very easy to leak oil; the hydroxypropyl starch and the oxidized hydroxypropyl starch have good viscosity and meet the production requirements, so that the hydroxypropyl starch or the oxidized hydroxypropyl starch are preferred.

Embodiment 6

Influence of Different Thicknesses of Gum Skins on Properties of Products
1) Gum Dissolving Process
8 KG of I-type (Iota) carrageenan (the weight-average molecular weight of the carrageenan was $1.50\pm0.1\times10^6$), 30 KG of hydroxypropyl starch, 15 KG of glycerin and 47 KG of purified water were weighed, put in a gum dissolving tank and heated to 80 to 90° C. to enable a gum solution to swell, then heat was preserved for 20 to 120 min, and degassing was performed until the gum solution was clear and transparent to obtain the gum solution.
2) Pill Rolling Process
A 22-minim cylindrical soft capsule mold was selected, a gum box of a pill rolling machine was heated to 80 to 95° C., a rotary drum was heated to 20 to 40° C., gum was supplied, the gum skins were set to be in different thicknesses, pill rolling was performed at a machine speed of 1.5 rpm, the content was linseed oil, pills were dried until the hardness of the gum pills met the requirement (50 to 70 N), and the pills were selected and finally packaged.

The gum skin joint rate, the content loading capacity, the oil leakage rate, the rupture time and hardness of soft capsules prepared from the gum skins in different thicknesses were detected, and the result is shown in Table 6.

TABLE 6

| Influence of Different Thicknesses of Gum Skins on Products | | | | | |
|---|---|---|---|---|---|
| Gum skin thickness | 0.20 | 0.30 | 0.45 | 0.60 | 0.80 |
| Gum skin joint rate | 70% | 70% | 70% | 70% | 70% |
| Content loading capacity | 750 mg | 1000 mg | 1000 mg | 950 mg | 850 mg |
| Oil leakage rate | 5% | Less than 1% | Less than 1% | Less than 1% | Less than 1% |
| Rupture time | 1 min | 3 min | 5 min | 13 min | 25 min |
| Hardness | 30N | 50N | 70N | 70N | 70N |

The data show that gum skins in the thickness of 0.30 mm to 0.60 mm can be prepared on the premise of meeting the above performance indexes. Theoretically, the thicker the gum skins, the better, but the thinner the gum skins are, the higher the risk of oil leakage is, so in order to control the oil leakage rate, the conventional gum skin thickness in the industry is 0.70 mm to 0.90 mm. However, by adjusting the formula of the soft capsules and combining the production process of the present disclosure, on the premise of ensuring the oil leakage rate of the products, the thickness of the gum skins can be 0.30 mm to 0.60 mm. When the thickness of the gum skins is large, the oil leakage rate of the capsules is low, but the rupture time is too long, and the cost of the gum skins is too high; when the thickness of the gum skins is too small, the rupture time is short, but the oil leakage rate of the capsules is high, the capsules are too soft, and the hardness is not enough. The preferred thickness of the gum skins is 0.30 mm to 0.60 mm by comprehensively considering the cost and the oil leakage rate.

Embodiment 7

Influence of Different Machine Speeds on Properties of Products
1) Gum Dissolving Process
8 KG of I-type (Iota) carrageenan (the weight-average molecular weight of the carrageenan was $1.50\pm0.1\times10^6$), 30 KG of hydroxypropyl starch, 15 KG of glycerin and 47 KG of purified water were weighed, put in a gum dissolving tank and heated to 80 to 90° C. to enable a gum solution to swell, then heat was preserved for 20 to 120 min, and degassing was performed until the gum solution was clear and transparent to obtain the gum solution.
2) Pill Rolling Process
A 22-minim cylindrical soft capsule mold was selected, a gum box of a pill rolling machine was heated to 80 to 95° C., a rotary drum was heated to 20 to 40° C., gum was supplied, the thickness of gum skins was set to be 0.40 mm, pill rolling was performed at different machine speeds, the content was linseed oil, pills were dried until the hardness of the gum pills met the requirement (50 to 70 N), and the pills were selected and finally packaged.

The gum skin joint rate, the content loading capacity and the oil leakage rate of soft capsules prepared at the different machine speeds were detected, and the result is shown in Table 7.

TABLE 7

| Influence of Different Machine Speeds on Products | | | | | |
|---|---|---|---|---|---|
| Machine speed | 1.5 rpm | 2.5 rpm | 3.0 rpm | 4.0 rpm | 5.0 rpm |
| Gum skin joint rate | 80% | 75% | 70% | 60% | 50% |
| Content loading capacity | 1000 mg | 1000 mg | 1000 mg | 1000 mg | 1000 mg |
| Oil leakage rate | Less than 1% | Less than 1% | Less than 1% | Less than 1% | Less than 1% |

Conventional plant soft capsule production considers the problem of the oil leakage rate, the machine speed is generally relatively low, and it can also be seen from the joint rate of a gum solution that a joint is relatively perfect and the risk of oil leakage is low. However, the production efficiency at a low speed is low, while a plant soft capsule production process of the present disclosure can achieve the approximate gum skin joint rate at the machine speed of 1.5 to 5.0 rpm, the oil leakage rate is less than 1%, and the plant soft capsule production process has extremely high production efficiency.

Embodiment 8

Influence of Different Ions on Properties of Products

1) Gum Dissolving Process

8 KG of I-type (Iota) carrageenan (the weight-average molecular weight of the carrageenan was $1.50\pm0.1\times10^6$), 30 KG of hydroxypropyl starch, 15 KG of glycerin, 0.1 KG of ions (if necessary) and 47 KG of purified water were weighed, put in a gum dissolving tank and heated to 80 to 90° C. to enable a gum solution to swell, then heat was preserved for 20 to 120 min, and degassing was performed until the gum solution was clear and transparent to obtain the gum solution.

2) Pill Rolling Process

A 22-minim cylindrical soft capsule mold was selected, a gum box of a pill rolling machine was heated to 80 to 95° C., a rotary drum was heated to 20 to 40° C., gum was supplied, the thickness of gum skins was set to be 0.40 mm, pill rolling was performed at a machine speed of 3.0 rpm, the content was linseed oil, pills were dried until the hardness of the gum pills met the requirement (50 to 70 N), and the pills were selected and finally packaged.

The gum skin joint rate, the content loading capacity, the oil leakage rate and the rupture time of soft capsules prepared from the different ions were detected, and the result is shown in Table 8.

TABLE 8

Influence of Different Ions on Products

| Ion | Sodium chloride | Potassium chloride | Calcium chloride | No ion |
| --- | --- | --- | --- | --- |
| Gum skin joint rate | 90% | 85% | 85% | 70% |
| Content loading capacity | 1000 mg | 1000 mg | 1000 mg | 1000 mg |
| Oil leakage rate | Less than 1% | Less than 1% | Less than 1% | Less than 1% |
| Rupture time | 18 min | 20 min | 25 min | 5 min |

In the existing technology, calcium chloride, potassium chloride, sodium chloride and other ions are used as film-forming agents to promote cross-linking of carrageenan so as to realize excellent film forming property and ensure the toughness of gum skins; and it is found in the study of the present disclosure that the addition of the film-forming agents results in too long capsule rupture time far exceeding 15 minutes. According to the present disclosure, the soft capsules with equivalent or even better performance (basically the same toughness as measured by the content loading capacity) can be prepared without adding any metal ions, and the rupture time is obviously shortened and completely meets the USP standards.

Embodiment 9

Influence of Different Pigments on Properties of Products

1) Gum Dissolving Process

8 KG of I-type (Iota) carrageenan (the weight-average molecular weight of the carrageenan was $1.50\pm0.1\times10^6$), 30 KG of hydroxypropyl starch, 15 KG of glycerin, 1 KG of pigments and 47 KG of purified water were weighed, put in a gum dissolving tank and heated to 80 to 90° C. to enable a gum solution to swell, then heat was preserved for 20 to 120 min, and degassing was performed until the gum solution was clear and transparent to obtain the gum solution.

2) Pill Rolling Process

A 22-minim cylindrical soft capsule mold was selected, a gum box of a pill rolling machine was heated to 80 to 95° C., a rotary drum was heated to 20 to 40° C., gum was supplied, the thickness of gum skins was set to be 0.40 mm, pill rolling was performed at a machine speed of 3.0 rpm, the content was linseed oil, pills were dried until the hardness of the gum pills met the requirement (50 to 70 N), and the pills were selected and finally packaged.

The result of properties of soft capsules prepared from the different pigments is shown in Table 9.

TABLE 9

Influence of Different Pigments on Products

| Pigment | Caramel | Annatto | Spirulina blue | Purple sweet potato red | Red iron oxide | Carmine |
| --- | --- | --- | --- | --- | --- | --- |
| Appearance | Brown | Orange | Blue | Purple red | Red brown | Red |
| Fade or not | Fade Not fade | Not fade | Not fade | Fade | Not fade | Not fade |
| Gum solution performance | Poor | Good | Good | Good | Poor | Good |

Because the production process of the plant soft capsule is high in temperature and conventional pigments are extremely easy to fade at high temperature, screening of the pigments with resistance to high temperature and meeting production requirements has extremely important significance. According to the present disclosure, the influence of various pigments on the performance of the gum solution was tested, and it is found that when the adding proportion of caramel is high, the viscosity of the gum solution is very strong, but the performance of the gum solution is poor, and the gum solution cannot be spread to form a film. Purple sweet potato red can meet production requirements, but this natural pigment is extremely easy to fade at high temperature. Although red iron oxide does not fade at high temperature, the gum solution has poor performance. After screening for many times, it is found that annatto and *spirulina* blue do not affect the performance of the gum solution, and do not fade at high temperature for a certain time, which is of great significance for enriching product types.

In Table 9, the purple sweet potato red (also known as a purple sweet potato red pigment) is a natural red pigment extracted from roots, stems and leaves of purple sweet potatoes, and the structure of the purple sweet potato red contains a plurality of phenolic hydroxyl groups. The stability of the purple sweet potato red pigment was studied in detail in the existing technology (Food Processing, No. 2, Vol. 41, 2016, pages 38-41, Research on Stability of Purple Sweet Potato Red Pigment), and the research shows that $Al^{3+}$, $Ca^{2+}$ and $Sn^{2+}$ are the best for the stability of the purple sweet potato red pigment, but the addition of metal ions in the system of the present disclosure has a great influence on the rupture time of the soft capsules. In addition, the article shows that the metal ion types may have an adverse effect on accelerating the color fading, so the reference significance is not great.

In order to develop a purple red soft capsule and solve the problem of discoloration of the purple sweet potato red during preparation of the soft capsule, different kinds of food additives were researched to serve as color fixatives of the purple sweet potato red, and it is found that meglumine can effectively solve the problem of fading of the purple sweet potato red; a preparation method of a soft capsule added with a color fixative differs from the screening method of the pigments in that the purple sweet potato red was selected as the pigment, the color fixative with the weight of 50 wt % (namely 500 g) of the purple sweet potato red was added, and the color of soft capsule shells prepared from different color fixatives was taken as a measure of the color fixative effects of the color fixatives. The result is shown in Table 9-A.

TABLE 9-A

Color Fixative effects of Different Color Fixatives

| | Color change of soft capsule shells at different stages | |
|---|---|---|
| Color fixative | 0 day | Accelerate for 3 months at 40° C. |
| ND | Basically colorless | — |
| Ascorbic acid | Basically colorless | — |
| Citric acid | Basically colorless | — |
| Glucose | Light purple | Basically colorless |
| L-cysteine hydrochloride | Purple red | Become dark red after two months |
| Meglumine | Purple red | Purple red |
| Sodium benzoate | Basically colorless | — |

Note: ND means that no color fixative is added as a contrast; '———' means not tested; 0 day refers to soft capsules prepared on the same day; accelerate for 3 months at 40° C. means that the prepared soft capsules are packaged by PVC plastic bottles (simulating commercial packages) and placed in the dark for 3 months at a temperature of $(40\pm2)°$ C., and the color change of the capsule shells is observed.

The experiment result shows that acid color fixatives (ascorbic acid and citric acid) and organic acid salts (sodium benzoate) basically have no color fixative effect on the purple sweet potato red in the system; glucose has a weak color fixative effect, only L-cysteine hydrochloride and meglumine have obvious color fixative effects, but only meglumine has an excellent long-term color fixative effect when an accelerated test is adopted for evaluating the long-term placement, and can really have the prospect of industrial application.

Embodiment 10

1) Gum Dissolving Process

8 KG of I type (Iota) carrageenan (the weight-average molecular weight of the carrageenan was $1.50\pm0.1\times10^6$), 30 KG of hydroxypropyl starch, 15 KG of glycerin and 47 KG of purified water were weighed, put in a gum dissolving tank and heated to 80 to 90° C. to enable a gum solution to swell, then heat was preserved for 20 to 120 min, and degassing was performed until the gum solution was clear and transparent to obtain the gum solution.

2) Pill Rolling Process

A 22-minim cylindrical soft capsule mold was selected, a gum box of a pill rolling machine was heated to 80 to 95° C., a rotary drum was heated to 20 to 40° C., the gum was supplied, the thickness of gum skins was set to be 0.40 mm, pill rolling was performed at a machine speed of 3.0 rpm, the content was linseed oil, pills were dried until the hardness of the gum pills met the requirement (50 to 70 N), and the pills were selected and finally packaged.

The rupture time of an obtained finished product is 5 min, an oil leakage rate is controlled to be less than 1%, and the process has extremely high production efficiency and meets the USP standards.

Embodiment 11

1) Gum Dissolving Process

3 KG of I type (Iota) carrageenan (the weight-average molecular weight of the carrageenan was $1.50\pm0.1\times10^6$), 40 KG of hydroxypropyl starch, 20 KG of glycerin and 37 KG of purified water were weighed, put in a gum dissolving tank and heated to 80 to 90° C. to enable a gum solution to swell, then heat was preserved for 20 to 120 min, and degassing was performed until the gum solution was clear and transparent to obtain the gum solution.

2) Pill Rolling Process

A 22-minim cylindrical soft capsule mold was selected, a gum box of a pill rolling machine was heated to 80 to 95° C., a rotary drum was heated to 20 to 40° C., the gum was supplied, the thickness of gum skins was set to be 0.40 mm, pill rolling was performed at a machine speed of 3.0 rpm, the content was linseed oil, pills were dried until the hardness of the gum pills met the requirement (50 to 70 N), and the pills were selected and finally packaged.

The obtained detection result is shown in Table 11:

TABLE 11

| Soft Capsule Detection Result | |
|---|---|
| Gum skin joint rate | 70% |
| Content loading capacity | 800 mg |
| Oil leakage rate | Less than 1% |
| Rupture time | 3 min |
| Hardness | 55N |

Embodiment 12

1) Gum Dissolving Process

15 KG of I type (Iota) carrageenan (the weight-average molecular weight of the carrageenan was $1.50\pm0.1\times10^6$), 20 KG of hydroxypropyl starch, 10 KG of glycerin and 55 KG of purified water were weighed, put in a gum dissolving tank and heated to 80 to 90° C. to enable a gum solution to swell, then heat was preserved for 20 to 120 min, and degassing was performed until the gum solution was clear and transparent to obtain the gum solution.

2) Pill Rolling Process

A 22-minim cylindrical soft capsule mold was selected, a gum box of a pill rolling machine was heated to 80 to 95° C., a rotary drum was heated to 20 to 40° C., the gum was supplied, the thickness of gum skins was set to be 0.40 mm, pill rolling was performed at a machine speed of 3.0 rpm, the content was linseed oil, pills were dried until the hardness of the gum pills met the requirement (50 to 70 N), and the pills were selected and finally packaged.

The obtained detection result is shown in Table 12:

TABLE 12

| Soft Capsule Detection Result | |
|---|---|
| Gum skin joint rate | 60% |
| Content loading capacity | 750 mg |
| Oil leakage rate | Less than 1% |
| Rupture time | 6 min |
| Hardness | 65N |

Although the embodiments of the present disclosure have been described in detail, it should be understood that various changes, substitutions and alterations can be made herein without departing from the spirit and scope of the present disclosure.

The invention claimed is:

1. A preparation method of plant soft capsules, comprising the following steps:

1) gum dissolving process:

weighing carrageenan, starch, a plasticizer, a pigment, and water in a formula amount to obtain a mixture, heating until the mixture swells at 80 to 90° C., preserving heat for 20 to 120 minutes, and degassing until the mixture is clear and transparent to obtain a gum solution; and 2) pill rolling process:

heating a gum box of a pill rolling machine at 80 to 95° C., heating a rotary drum at 20 to 40° C., supplying the gum solution to the pill rolling machine, setting a thickness of a gum skin to be 0.30 to 0.60 mm, rolling the gum solution to obtain the plant soft capsules after setting a machine speed of the pill rolling machine, drying until the plant soft capsules reach a certain hardness, selecting the plant soft capsules, and finally packaging the plant soft capsules, wherein the weight-average molecular weight Mw of the carrageenan is $1.2 \times 10^6$ to $2.0 \times 10^6$ daltons, and the carrageenan is an iota-carrageenan or a combination of the iota-carrageenan and the kappa-carrageenan; and in the combination of the iota-carrageenan and the kappa-carrageenan, the iota-carrageenan:the kappa-carrageenan is calculated to be 9.9:0.1 to 7.0:3.0 according to weight ratio, wherein the plasticizer is selected from the group consisting of glycerin and sorbitol, wherein the starch is selected form the group consisting of hydroxypropyl starch and oxidized hydroxypropyl starch, and wherein the pigment is selected from the group consisting of annatto and *spirulina* blue.

\* \* \* \* \*